(12) United States Patent
Henckel

(10) Patent No.: US 7,893,030 B2
(45) Date of Patent: Feb. 22, 2011

(54) STABLE CHROMOGENIC TEST REAGENT AND ITS USE IN COAGULATION-DIAGNOSTIC TESTS

(75) Inventor: Thilo Henckel, Wetter (DE)

(73) Assignee: Siemens Healthcare Diagnostics Products GmbH, Marburg (DE)

( * ) Notice: Subject to any disclaimer, the term of this patent is extended or adjusted under 35 U.S.C. 154(b) by 800 days.

(21) Appl. No.: 11/335,630

(22) Filed: Jan. 20, 2006

(65) Prior Publication Data

US 2006/0166301 A1 Jul. 27, 2006

(30) Foreign Application Priority Data

Jan. 21, 2005 (DE) .................. 10 2005 003 145

(51) Int. Cl.
*A61K 38/36* (2006.01)
(52) U.S. Cl. .................................. 514/13.6; 514/14.7
(58) Field of Classification Search ........................ None
See application file for complete search history.

(56) References Cited

U.S. PATENT DOCUMENTS

| | | | |
|---|---|---|---|
| 4,409,327 A | 10/1983 | Bartl et al. | |
| 4,480,030 A | 10/1984 | Svendsen et al. | |
| 4,508,644 A | 4/1985 | Heber et al. | |
| 4,598,043 A * | 7/1986 | Svendsen | 435/13 |
| 4,769,318 A * | 9/1988 | Hamasaki et al. | 435/2 |
| 5,320,945 A | 6/1994 | Dessauer et al. | |
| 5,478,810 A * | 12/1995 | Stuber et al. | 514/17 |
| 6,492,494 B1 * | 12/2002 | Cederholm-Williams | 530/381 |

FOREIGN PATENT DOCUMENTS

| | | |
|---|---|---|
| EP | 034 122 A1 | 9/1983 |
| EP | 078 764 A1 | 1/1986 |
| EP | 0 408 075 A2 | 1/1991 |
| EP | 0 420 332 B1 | 4/1995 |
| EP | 0 456 152 B1 | 10/1997 |
| EP | 0 802 986 B1 | 9/2001 |
| EP | 1 367 135 A1 | 12/2001 |
| EP | 1367135 A1 * | 12/2003 |
| WO | WO-96/21740 | 7/1996 |

OTHER PUBLICATIONS

H.C. Hemker et al, "Continuous Registration of Thrombin Generation in Plasma, Its Use for the Determination of the Thrombin Potential," *Thrombosis and Haemostasis*, 70:617-624 (1993).
T. A. Tomaszek, Jr. et al., "Chromophoric Peptide Substrates for the Spectrophotometric Asay of HIV-1 Protease," *Biochemical and Biophysical Research Communications*, 168 (I): 274-280 (1990).
Chromogenix Instrumentation Laboratory: "S-2772™" product Information, according to European Search Report (2003).
Chromogenix Instrumentation Laboratory: "Coamatic® LR Antithrombin" product information, according to European Search Report (2003).
Pentapharm: "Pefachromee® PAP (Pefa-5920)" product information, according to European Search Report (2003).

* cited by examiner

*Primary Examiner*—Christina Bradley
(74) *Attorney, Agent, or Firm*—Finnegan, Henderson, Farabow, Garrett & Dunner, L.L.P.

(57) ABSTRACT

The present invention relates to a chromogenic test reagent which comprises a chromogenic peptide substrate and an inhibitor of fibrin polymerization, which is particularly suitable for being used in coagulation-diagnostic tests and which is distinguished by the fact that it exhibits a nigh degree of stability and/or a long shelf life in the liquid state.

14 Claims, 3 Drawing Sheets

STABLE CHROMOGENIC TEST REAGENT AND ITS USE IN COAGULATION-DIAGNOSTIC TESTS

This application claims the benefit of priority of German Patent Application No. 10 2005 003 145.5, filed Jan. 21, 2005, and which is incorporated by reference herein.

The present invention relates to a chromogenic test reagent which is particularly suitable for being used in coagulation-diagnostic tests and which, in the liquid state, exhibits a high degree of stability and/or a long shelf life.

A large number of diagnostic tests are based on using chromogenic substrates. Chromogenic peptide substrates which are composed of a specific oligopeptide or polypeptide moiety and a chromophore (dye carrier) moiety are customarily used for determining factors possessing protease activity, for example for determining coagulation factors in blood and plasma samples. The chromogenic peptide substrate, which is initially colorless, is cleaved, in dependence on the quantity or activity of the proteolytic factor which is present in the sample, thereby releasing the chromophore, which can then be measured photometrically. The patent documents EP 34 122 A1 and U.S. Pat. No. 4,508,644, which is fully incorporated by reference herein, describe a large number of chromogenic peptide substrates and their use in diagnostic tests, for example for determining the coagulation factors factor IIa (thrombin) and factor Xa. The document EP 78 764 A1 describes a chromogenic method for determining the coagulation factor XIIa.

Para-nitroaniline (pNA) or 5-amino-2-nitrobenzoic acid (ANBA), whose yellow color can be measured at a wavelength of $\lambda=405$ nm, are examples of chromophores which are particularly frequently employed.

In coagulation diagnostics, the determination of the activity of enzymically active factors in blood or plasma samples is usually carried oat under conditions which are as physiological as possible. It is particularly important to make sure of having a physiological pH of about 7.4 in the test assay. In order to prevent any pH changes in the test assay, the rest substances which have to be mixed with the blood or plasma sample are usually dissolved in buffers having a neutral to slightly alkaline pH.

However, the disadvantage of such a test design is that the stability of some test components is reduced in neutral to alkaline medium. Thus, pNA, for example, breaks down more rapidly at a pH of >6.0. The resulting yellow coloration of the pNA substrate solution makes any further use of the solution, or a reliable evaluation of the test, impossible. For this reason, pNA substrates are usually lyophilized for long-term storage and only dissolved in a neutral liquid when required. In order to prevent pNA substrates decomposing in solutions, it is known to adjust the pH of the substrate solution to an acid value.

While it is necessary, in the case of a variety of chromogenic coagulation tests, to activate the blood coagulation cascade, thereby forming thrombin, or to add thrombin directly to the test assay, it is at the same time necessary to prevent the formation of a fibrin clot in order to avoid turbidity which would impair the photometric measurement of the sample. This can be contrived, for example, by using inhibitors of fibrin polymerization in the test assay. These inhibitors, which are termed clot inhibitors, are frequently oligopeptides which inhibit the polymerization of the fibrin monomers, which are formed under the influence of thrombin, and thereby prevent clot formation (see, for example, EP 0 456 152 B1).

Simple manipulation and a shelf life which is as long as possible are some of the criteria which are to be taken into account when developing reagents which provide the components which are required for a test method. Particular preference is given to liquid reagent formulations which are stable over a long period since errors, which can have a negative effect on the quality of the overall test method, can arise when the user reconstitutes lyophilized components.

The present invention was based on the object of providing a reagent which is stable over a long period, particularly in the liquid state, and which contains both a chromogenic peptide substrate and a clot inhibitor and which is consequently particularly suitable for being used in chromogenic coagulation tests which are evaluated photometrically.

The object is achieved by providing the methods and articles according to the invention which are described in the claims.

The present invention essentially relates to a preparation which comprises a chromogenic peptide substrate and an inhibitor of fibrin polymerization and which is further characterized by the fact that its pH is between 3.0 and 6.0, preferably between 4.0 and 5.0. In a particularly preferred embodiment, the pH of the reagent is 4.6±0.1.

In order to adjust the pH, proton donors, i.e. acids or their salts, are added to the liquid aqueous preparation. It is possible to use inorganic or organic acids or proton donors. A suitable buffer system may be necessary in order to ensure a stable pH and in order, for example, to prevent any alkalinization by carbon dioxide.

A particularly preferred embodiment of a preparation according to the invention comprises acetate ions ($CH_3COO^-$). The present invention therefore also relates to a method for preparing a test reagent, wherein a chromogenic peptide substrate and an inhibitor of fibrin polymerization are combined and the pH of the reagent is adjusted with acetic acid to a value of between 3.0 and 6.0, preferably to a value of between 4.0 and 5.0, particularly preferably to a value of 4.6±0.1.

Surprisingly, a preparation according to the invention in the liquid state is more stable, and consequently able to be stored for a longer period, than an equivalent preparation having a neutral pH in the liquid or lyophilized state.

It was observed that a preparation according to the invention in the liquid state exhibited a measured value deviation from the initial value of not more than 10% over a period of 60 weeks at a storage temperature of 4° C. The initial value is to be understood as being the measured value, or the test result, which was determined when using the preparation as a test reagent in a suitable test method on the day on which the preparation was prepared. An ETP test (see EP 0 420 332 B1 or example 2 below) is, for example, suitable for being used as a method for determining the stability of a reagent which, for example, contains a chromogenic peptide substrate which is cleaved by thrombin.

Chromogenic peptide substrates within the meaning of the present invention are composed of a specific oligopeptide or polypeptide moiety to which a chromogenic group, i.e. a colored or fluorescent group which can be cleaved off, is coupled, with the chromogenic group exhibiting, after having been cleaved off from the peptide substrate, optical properties which are different from those of the uncleaved chromogenic peptide substrate and which can be measured by means of absorption spectrophotometry or fluorescence spectrophotometry. Examples of chromogenic groups which can be coupled to a peptide substrate are para-nitroaniline (pNA), 5-amino-2-nitrobenzoic acid (ANBA), 7-amino-4-methoxycoumarin (ANC), quinonylamide (QUA), dimethyl 5-aminoisophthalate (DPA) and their derivatives.

The oligopeptide or polypeptide moiety of the chromogenic peptide substrate can be selected from the large number of substrates, which are known to the skilled person, which are cleaved by the coagulation factor to be determined such as factor X/Xa or thrombin. In a preferred embodiment, the reagent contains a chromogenic peptide substrate which is recognized and converted by thrombin, such as a peptide substrate having the sequence Ala-Gly-Arg-$R_1$ or the sequence Gly-Gly-Arg-$R_1$, with $R_1$ being a chromogenic group. Particularly preferred peptide substrates which are recognized and converted by thrombin are, for example, the pNA-coupled peptide substrate Ala-Gly-Arg-pNA (PEFACHROME®TG, Pentapharm Ltd., Basle, Switzerland) or the AMC-coupled peptide substrate Gly-Gly-Arg-AMC (Bachem). Other suitable peptide substrates which are cleaved by thrombin are those of the general formula Msc-Val-Xaa-$R_1$, in which Msc is methylsulfonyl-ethyloxycarbonyl, Val is the amino acid valine and Xaa is an amino acid residue, which comprises a terminal guanidino group or ureido group which is separated from the peptide backbone by at least two carbon atoms, and in which $R_1$ is a chromogenic group, with the peptide Msc-Val-Arg-$R_1$ or Msc-Val-Arg-pNA being particularly preferred (EP 0 802 986 B1). Other examples of chromogenic peptide substrates having specificities for different proteases can be found, for example, in U.S. Pat. No. 4,508,644.

In a preferred embodiment, the preparation can additionally comprise one or more stabilizers such as bovine serum albumin, chaotropic salts, chaperones and chaperone-like substances, dextran and other sugars.

Suitable inhibitors of fibrin polymerization are peptides, particularly preferably those having the general peptide sequence GPRP-X—$NH_3$, (SEQ ID NO: 1) where G is the amino acid glycine, P is the amino acid L-proline, R is the amino acid L-arginine and X is alanine or glycine (see EP 0 456 152 B1).

The invention also relates to the use of the preparation according to the invention as a test reagent in a test method for determining a coagulation parameter in a whole blood or plasma sample. Whole blood or plasma of human or animal origin is, suitable sample material. Platelet-poor or platelet-rich plasma, to which EDTA and/or citrate may be added, is particularly suitable.

Preference is given to using a preparation according to the invention as a test reagent in a test method for determining the generation of thrombin in blood or plasma. Examples of these test methods are described in the patent documents EP 1 367 135 A1 and EP 0 420 332 B1. Particular preference is given to using the reagent according to the invention in a test method for determining the endogenous thrombin potential (ETP) and other coagulation parameters which can be calculated from the thrombin formation curve or which can be derived from the measured turnover kinetics of a chromogenic thrombin substrate [see ER 0 420 332 B1, EP 0 802 986 B1 and Hemker et al. (1993) Thromb. Haemostatis 70: 617-624].

Preference is furthermore given to using a preparation according to the invention as test reagent in chromogenic tests for determining the coagulation time, for example in a chromogenic prothrombin time (PT) coagulation test as described in the patent document EP 0 014 039 A1.

The invention also relates to a test kit for carrying out a chromogenic test method, with the rest kit comprising at least one preparation which contains a chromogenic peptide substrate and an inhibitor of fibrin polymerization and has a pH of between 3.0 and 6.0. The preparation can be provided as a liquid reagent or as a lyophilizate which can be reconstituted in water or buffer. A preferred test kit for use in a coagulation-diagnostic test method additionally comprises one or more coagulation activators. In order, for example, to induce the formation of thrombin, the test kit can comprise, e.g., solutions or lyophilizates which contain $Ca^{2+}$ ions, thromboplastin or contact activators, such as kaolin, phospholipids, snake venom, or thrombomodulin and activated protein C.

BRIEF DESCRIPTION OF THE DRAWINGS

Figures

FIG. 1: Storage of the preparations at +4° C.

FIG. 2: Storage of the preparations at room temperature.

FIG. 3: Storage of the preparations at +37° C.

Figure 1:
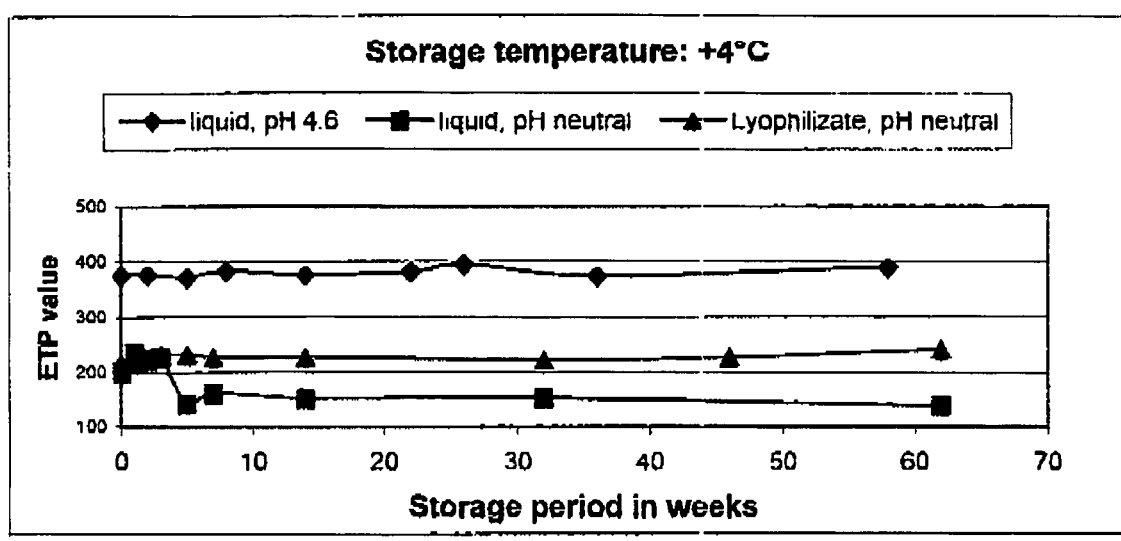
FIGS. 1 to 3 are plots depicting test results (absolute measured values) which were obtained using an acidic liquid preparation according to the invention (pH 4.6) or using neutral preparations (pH 7.4).

The following examples serve to illustrate the invention and are not to be understood as being limiting.

EXAMPLES

Example 1

Preparing a Reagent According to the Invention

In order to prepare a test reagent according to the invention which was suitable for being used in a method for determining thrombin activity, freeze-dried H-β-Ala-Gly-Arg-pNA.2AcOH, as chromogenic thrombin substrate (PEFACHROME®TG, Pentapharm Ltd., Basle, Switzerland), freeze-dried H-Gly-Pro-Arg-Pro-Ala-$NH_2$ (as the trifluoroacetic acid salt), as clot inhibitor, NaCl, bovine serum albumin and dextran were dissolved in demineralized water and the pH of the solution was adjusted with acetic acid to a value of 4.6±0.1. The reagent was finally transferred to a sealable reagent container and stored in the liquid state.

Reagents having a neutral pH were prepared for purposes of comparison. For this, freeze-dried Msc-Val-Arg-pNA.2HCl, as chromogenic thrombin substrate (Neosystem Groupe SNPE, Strasbourg, France) and freeze-dried H-Gly-Pro-Arg-Pro-Ala-$NH_2$ (SEQ ID NO: 2) (as the trifluoroacetic acid salt), as clot inhibitor, NaCl, tris/HCl, bovine serum albumin and dextran were dissolved in demineralized water and the pH was adjusted to 7.4. One part of this neutral reagent was transferred to a sealable reagent container and stored in the liquid state while the other part was transferred to a lyophilization receptacle, freeze-dried and stored as a lyophilizate.

Example 2

Using a Reagent According to the Invention in a Test Method for Determining the Endogenous Thrombin Potential (ETP) After Long-Term Storage Under Different Conditions In order to examine the stability of the acidic liquid reagent according to the invention, aliquots of the reagent were stored for up to 96 weeks at 4° C., at room temperature (RT, 15-25° C.) or at 37° C. and employed in an ETP test after different periods of storage. An analogous procedure was adopted with the two neutral control reagent formulations.

A batch of deep-frozen, platelet-poor human plasma (normal plasma pool), an aliquot of which was thawed at each respective rest time point, was used as the sample material in all the experiments.

The acidic reagent according to the invention was used to carry out an ETP test in the following manner:

135 µl of plasma were first of all mixed with 40 µl of buffer (50 mM tris-HCl, pH 7.4). 40 µl of the reagent according to the invention were then added. After a 7-minute incubation, 15 µl of CaCl$_2$ (250 mM) and 30 µl of Innovin® (reagent consisting of recombinant human tissue factor and a mixture of synthetic phospholipids; Dade Behring Marburg GmbH, Marburg, Germany) were added to the mixture in order to activate the formation of thrombin. The absorption of the test mixture was measured continuously at a wavelength of $\lambda=405$ nm over a period of 20 minutes. The turnover kinetics, which were determined in this way, of the chromogenic thrombin substrate were then used to determine the ETP value of the sample employing an analytical method which is described in patent application DE 10 2004 059 055.9.

A mixing of the reagents with the sample, the measurement of the absorption, and the automatic determination of the ETP value, were carried out in a fully automated manner on a BCS® coagulation analyzer (Dade Behring Marburg GmbH, Marburg, Germany).

The neutral control reagents were used to carry out an ETP test in the following manner (see also EP 0 420 332 B1):

The lyophilized reagent was dissolved freshly at each respective test time point using demineralized water. 200 µl of plasma were mixed with 80 µl of the liquid neutral reagent or with 80 µl of the freshly reconstituted lyophilized reagent. After a 7-minute incubation, 30 µl of CaCl$_2$ (250 mM) and 60 µl of Innovin® (Dade Behring Marburg Gmbh, Marburg, Germany) were added to the mixture in order to activate the formation of thrombin. Measurement of the absorption and determination of the ETP value were effected as described above.

Figure 2:
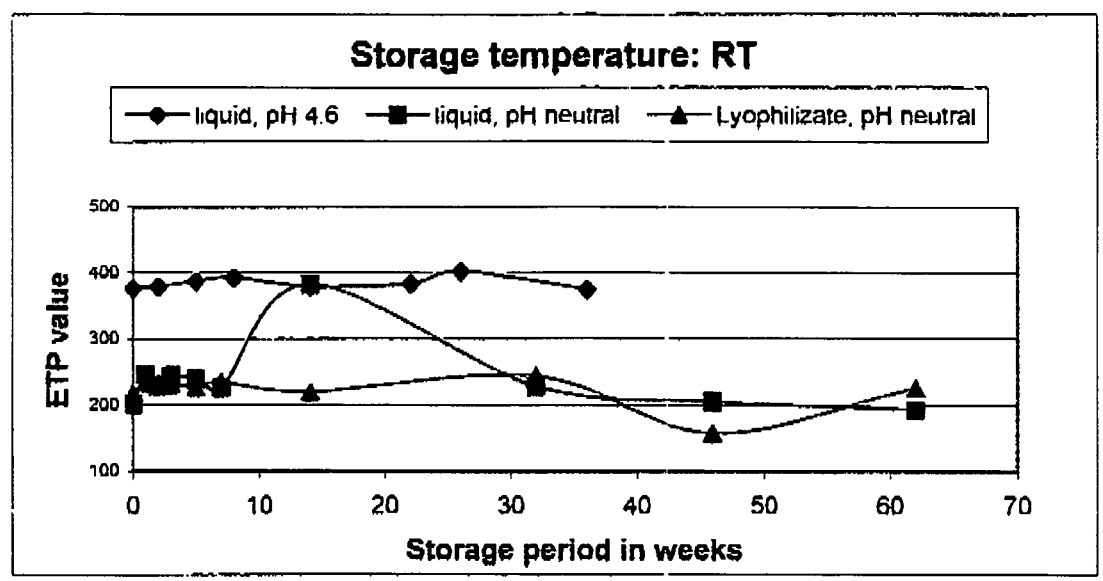
Figure 3:
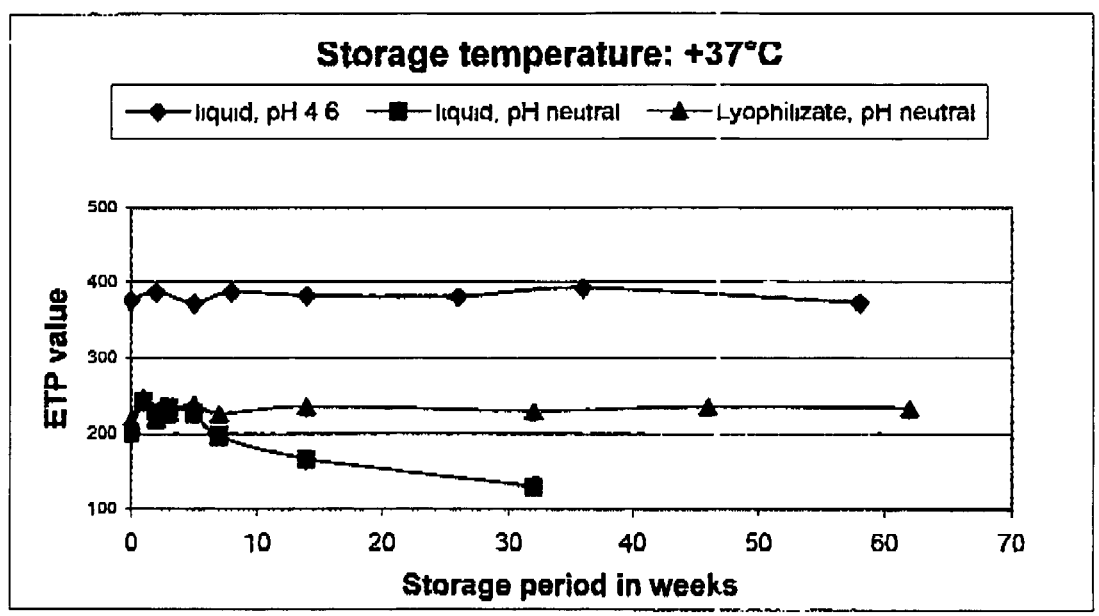

The test results are plotted in FIGS. 1 to 3 in dependence on the period during which the reagents were stored at the different storage temperatures of 4° C. (FIG. 1), room temperature (15-25° C.) (FIG. 2) and, respectively, 37° C. (FIG. 3).

As can be seen from the figures, the reagent formulation according to the invention exhibits a high degree of stability over a period of up to 60 weeks. At all the storage temperatures, and at each time point, the maximum divergence from the initial value, which was measured at the time point t=0 (day of preparation), is markedly less than 10% and in the main even less than 5%. After 60 weeks of storage at 4° C., the lyophilized neutral reagent formulation shows a divergence of the measured value from the initial value of more than 10% and, at a higher storage temperature (37° C.), the measured value already diverges by up to 15% after 4 weeks. The liquid neutral reagent formulation exhibits very large variations of up to more than 20% at all the storage temperatures and is therefore unstable. The shelf life of the liquid neutral reagent is limited to one or at most two days.

Table 1 lists the percentage divergences, from the respective value which was initially measured at the time point to, of the different reagent formulations in dependence on the different storage conditions. The different reagent formulations were stored over a period of up to 96 weeks at from 2 to 8° C., at room temperature or, respectively, at 37° C. At a storage temperature of from 2 to 8° C., the measured values which were determined using a preparation according to the invention (liquid, pH 4.6) do not diverge by more than 5% over the entire period. At all the storage temperatures investigated, the acidic liquid preparation exhibits the smallest divergences and consequently the highest degree of stability. In the case of the neutral liquid preparation (liquid, pH 7.4), the reagent could be seen to become increasingly yellow with increasing length of storage at room temperature or at 37° C.

TABLE 1

| Storage temperature [° C.] | | Divergence from the initial value in percent [%] Time t [weeks] | | | | | | | | | | | |
|---|---|---|---|---|---|---|---|---|---|---|---|---|---|
| | | 1 | 2 | 5 | 7 | 8 | 14 | 26 | 32 | 36 | 46 | 58 | 82 | 96 |
| 2-8° C. | liquid, pH 4.6 | | 0 | 1 | | −2 | 0 | −5 | | 0 | | −4 | 3 | 0 |
| | liquid, pH neutral | −17 | −12 | 29 | 20 | | 25 | | 24 | | | | | |
| | lyophilizate, pH neutral | −2 | −3 | −8 | −5 | | −5 | | −2 | | −5 | | | |
| Room temperature | liquid, pH 4.6 | | −1 | −3 | | −5 | −1 | −7 | | 0 | | | | |
| | liquid, pH neutral | −22 | −14 | −19 | −13 | | −90 | | −13 | | −2 | | | |
| | lyophilizate, pH neutral | −9 | −7 | −5 | −8 | | −2 | | −12 | | 27 | | | |
| 37° C. | liquid, pH 4.6 | | −3 | 1 | | −3 | −2 | −1 | | −4 | | 1 | | |
| | liquid, pH neutral | −20 | −13 | −13 | 2 | | 18 | | 36 | | | | | |
| | lyophilizate, pH neutral | −14 | −1 | −10 | −4 | | −8 | | −6 | | −8 | | | |

What is claimed is:

1. A composition comprising:

a) a chromogenic peptide substrate, wherein the chromogenic peptide substrate comprises a substrate of thrombin, and wherein the chromogenic group is selected from para-nitroaniline (pNA), 5-amino-2-nitrobenzoic acid (ANBA), 7-amino-4-methoxycoumarin (AMC), quinonylamide (QUA), dimethyl 5-aminoisophthalate (DPA), and their derivatives; and b) an oligopeptide inhibitor of fibrin polymerization, wherein the oligopeptide inhibitor of fibrin polymerization:
   i. inhibits polymerization of fibrin monomers which are formed under the influence of thrombin; and
   ii. comprises the peptide sequence GPRP-X—$NH_2$ (SEQ ID NO: 1), wherein G is the amino acid glycine, P is the amino acid L-proline, R is the amino acid L-arginine, and X is selected from the amino acids alanine and glycine; and wherein the pH of the composition is between 3.0 and 6.0.

2. The composition as claimed in claim 1, further comprising acetate ions.

3. The composition as claimed in claim 1, wherein the chromogenic peptide substrate is a para-nitroaniline-coupled peptide substrate.

4. The composition as claimed in claim 1, wherein the chromogenic peptide substrate is a 5-amino-2-nitrobenzoic acid-coupled peptide substrate.

5. The composition as claimed in claim 1, wherein the chromogenic peptide substrate comprises the sequence Ala-Gly-Arg-$R_1$, wherein $R_1$ is the chromogenic group.

6. The composition as claimed in claim 1, wherein the chromogenic peptide substrate comprises the sequence Msc-Val-Arg-$R_1$, wherein Msc is methylsulfonylethyl-oxycarbonyl and $R_1$ is the chromogenic group.

7. The composition as claimed in claim 1, further comprising one or more stabilizers.

8. A method for preparing the composition as claimed in claim 1, comprising the steps of:
   combining the chromogenic peptide substrate and the oligopeptide inhibitor of fibrin polymerization; and
   adjusting the pH to between pH 3.0 and 6.0 by adding a proton donor.

9. The method as claimed in claim 8, wherein the proton donor is acetic acid.

10. A method for determining a coagulation parameter in a whole blood or plasma sample, comprising:
   (a) adding to the whole blood or plasma sample the composition as claimed in claim 1;
   (b) determining the chromogenic signal of the chromogenic peptide substrate; and
   (c) calculating the coagulation parameter based upon the chromogenic signal of the chromogenic peptide substrate.

11. The method of claim 10, wherein the coagulation parameter is thrombin generation.

12. The method of claim 10, wherein the coagulation parameter is the endogenous thrombin potential of the sample.

13. The method of claim 11, wherein the coagulation parameter is the coagulation time of the sample.

14. The composition as claimed in claim 1, wherein the pH of the composition is between 3.0 and 5.0.

* * * * *

UNITED STATES PATENT AND TRADEMARK OFFICE
CERTIFICATE OF CORRECTION

PATENT NO. : 7,893,030 B2  
APPLICATION NO. : 11/335630  
DATED : February 22, 2011  
INVENTOR(S) : Thilo Henckel It is certified that error appears in the above-identified patent and that said Letters Patent is hereby corrected as shown below:

On the Title Page, Item (57), in the Abstract, line 5, "nigh degree" should read --high degree--.

In claim 6, column 7, lines 24-25, "Msc-VaI-Arg-$R_1$," should read --Msc-Val-Arg-$R_1$,--.

Signed and Sealed this  
Sixteenth Day of August, 2011

David J. Kappos  
*Director of the United States Patent and Trademark Office*